(12) United States Patent
Vassal et al.

(10) Patent No.: US 12,714,606 B2
(45) Date of Patent: Aug. 25, 2026

(54) MOISTURE SENSOR

(71) Applicant: LINXENS HOLDING, Mantes la Jolie (FR)

(72) Inventors: Simon Vassal, Mantes-la-Jolie (FR); Valerie Mousque, Mantes-la-Jolie (FR); Francois Germain, Mantes-la-Jolie (FR); Sebastien Prunier, Mantes-la-Jolie (FR)

(73) Assignee: LINXENS HOLDING, Mantes-la-Jolie (FR)

( * ) Notice: Subject to any disclaimer, the term of this patent is extended or adjusted under 35 U.S.C. 154(b) by 319 days.

(21) Appl. No.: 18/683,661

(22) PCT Filed: Sep. 23, 2022

(86) PCT No.: PCT/FR2022/051790
§ 371 (c)(1),
(2) Date: Sep. 12, 2024

(87) PCT Pub. No.: WO2023/052711
PCT Pub. Date: Apr. 6, 2023

(65) Prior Publication Data

US 2025/0025348 A1 Jan. 23, 2025

(30) Foreign Application Priority Data

Sep. 30, 2021 (FR) ....................................... 2110303

(51) Int. Cl.
*A61F 13/00* (2024.01)

(52) U.S. Cl.
CPC .............................. *A61F 13/00055* (2013.01)

(58) Field of Classification Search
CPC ................................................ A61F 13/00055
See application file for complete search history.

(56) References Cited

U.S. PATENT DOCUMENTS 3,559,052 A * 1/1971 Fathauer .............. G01N 27/223 324/670
4,408,128 A * 10/1983 Fujita .................. G01R 15/005 324/132

(Continued)

FOREIGN PATENT DOCUMENTS

EP 2014267 A1 1/2009
EP 2944299 A1 11/2015
WO 2013114273 A1 8/2013

OTHER PUBLICATIONS

International Search Report and Written Opinion of the International Searching Authority for related International Application No. PCT/FR2022/051790, dated Jan. 3, 2023, 15 pages.

*Primary Examiner* — Paresh Patel
(74) *Attorney, Agent, or Firm* — DITTHAVONG, STEINER & MLOTKOWSKI

(57) ABSTRACT

The present invention relates to a moisture sensor comprising a support substrate having a first face and a second face, geometrically opposite to the first face, and wherein: the first face is provided with a plurality of pairs of electrodes configured to be in contact with a liquid, and the second face comprises a plurality of means of detection connected to each other in parallel, and each means of detection comprises a transistor associated to a pair of electrodes, and the moisture sensor is sensitive to an equivalent resistance of the plurality of means of detection.

20 Claims, 5 Drawing Sheets

(56) References Cited

U.S. PATENT DOCUMENTS

| | | | | |
|---|---|---|---|---|
| 2011/0109325 | A1* | 5/2011 | Huang | G01N 11/00<br>324/656 |
| 2014/0253150 | A1* | 9/2014 | Menzel | G01R 27/2605<br>324/694 |
| 2016/0169881 | A1* | 6/2016 | Nazareth | G01N 33/54388<br>436/501 |
| 2019/0192066 | A1* | 6/2019 | Schoess | A61B 5/1109 |
| 2020/0405546 | A1* | 12/2020 | Naito | G01N 27/04 |
| 2021/0333308 | A1* | 10/2021 | Franceschini | G01R 1/06766 |

* cited by examiner

MOISTURE SENSOR

RELATED APPLICATION

This U.S. National Phase application claims priority to International Application No. PCT/FR2022/051790, entitled “Moisture Sensor,” filed Sep. 23, 2022, the entire contents of which is hereby incorporated by reference.

FIELD OF THE INVENTION

The present invention relates to a moisture sensor intended to detect the presence and position of a liquid on a surface.

BACKGROUND

The liquid comes from a point of origin, the moisture sensor makes it possible to measure the extent of the flow in a plane.

Thanks to a system of specially-selected electrodes and electronic components, it is possible to detect the location of a liquid on any given surface. There are many applications: leak detection, smart clothing, wound dressings, nappies, level sensors, mobility (cars, boats, etc.).

In particular, the present invention is particularly suitable for integration into a wound dressing for a chronic wound, wherein the healing process may take up to 12 months or even 18 months.

The wounds ooze a liquid, called exudate that contains—among others—water and electrolytes. This liquid, or exudate, gradually saturates the wound dressing. When the wound dressing reaches a certain level of saturation, the wound dressing must be changed. The wound dressing may be changed at regular intervals. However, when the saturation level is not reached, the change of wound dressing incurs costs (related to the cost of the nursing staff and the wound dressing) and a ventilation of the wound, that would be advantageous to avoid.

This is why, it is known from the prior art to equip the wound dressings with moisture-sensing systems to deduce the saturation state of the wound dressing. Among others, WO 2013/114273 is known to evaluate the saturation of a wound dressing by measuring the variation in electrical conductivity between two successive electrodes of a wound dressing moisture detection system. Such a system for detecting the moisture of the wound dressing is therefore dependent on the electrical conductivity of the liquid. This system does not adapt well to the differences in electrical conductivity of the different fluids that can be exuded (blood, pus, etc.) that depend on the pathology, the wound and the patient’s physiological data.

Moisture sensors described in the documents EP 2 014 267, EP 2 944 299, and US 2020/405546 are also known from the prior art.

BRIEF SUMMARY OF THE DISCLOSURE

The aim of the present invention is to provide a moisture sensor that is an improvement on those known in the prior art.

The aim of the present invention is achieved by means of a moisture sensor comprising a support substrate having a first face and a second face that is geometrically opposite to the first face. The first face is provided with a plurality of pairs of electrodes configured to be in contact with a liquid. The second face comprises a plurality of first means of detection connected to each other in parallel, and each first means of detection comprises a transistor associated with a pair of electrodes. Said transistor of each first means of detection is configured to switch from a first state to a second state when an electric current passes between electrodes of the pair of electrodes associated to the transistor. An electrode of the pair of electrodes is electrically connected in series to an input electrode of the transistor and the other electrode of the pair of electrodes is electrically connected to a fixed potential, in particular, to an earthed potential, and an output electrode of the transistor being electrically connected in series with a first resistor, such that the moisture sensor is sensitive to the equivalent resistance of said first resistors of the plurality of the first means of detection.

Thus, moisture detection is not directly achieved from the measurement of the resistance, impedance or electrical conductivity of the liquid in contact with the electrodes.

In the present invention, it is not necessary to measure the variation in resistance across the electrodes of each pair of electrodes, the electric current flowing through the pair of electrodes being used to make the transistors switch, or not. The electric current is induced by the presence of conductive liquid across the terminals of the electrodes, independently of the specific properties of the liquid. Moisture detection is thus based on a number of switched transistors, said transistors being switchable between two states.

From the equivalent resistance, it is possible to deduce the number of first resistors associated to each transistor that has been switched by the presence of liquid between the electrodes of a pair of electrodes. Thus, it is possible to deduce the number of pairs of electrodes connected by the presence of liquid between the electrodes of the pair of electrodes. The number of pairs of electrodes connected is relative to the wetted surface. The equivalent resistance according to the present invention is therefore correlated with the presence of liquid between the electrodes of the first face.

As a result, the present invention advantageously makes it possible to avoid the need to measure the resistance (or the impedance or electrical conductivity) of the liquid, that depends on the composition and properties specific to each liquid, in particular, to each exudate in the case of an application of the moisture sensor in a wound dressing.

In particular, the moisture sensor may be configured to measure the equivalent resistance of the first resistors of the plurality of the first means of detection.

More specifically, the moisture sensor may comprise an integrated circuit or a microchip, in particular, to measure the equivalent resistance and, optionally, to process the data measured.

On the other hand, the moisture sensor may be an electrical device that may comprise at least one computing unit and/or one processor. In addition to, or instead of the computing unit and/or processor, the moisture sensor may comprise an embedded computer.

By means of the computing unit and/or the processor and/or the integrated computer, the moisture sensor may be configured to measure the equivalent resistance of the first resistors of the plurality of the first means of detection.

The moisture sensor could also be configured to determine the voltage across the first resistors. In this case, when a voltage is measured, the moisture sensor may further comprise amplifying means in order to amplify the measured voltage before it is processed by a computing unit, a processor and/or an integrated computer.

The moisture sensor may also comprise data storage means. The storage medium may be selected by the person skilled in the art from among the known storage media, e.g., according to their capacity and speed. For example, measured equivalent resistance and/or obtained voltage values may be stored in these data storage means.

In addition, it should be noted that the connection of one of the electrodes to a fixed potential makes it easier to determine the number of transistors switched in one of said states compared to those switched in the other state.

In particular, the connection of one electrode to a fixed potential and the connection of the other electrode in series to the input electrode of the transistor makes it possible to obtain a variation of voltage in stages, facilitating the moisture detection.

The moisture sensor according to the present invention may be further improved, thanks to the following embodiments.

According to one embodiment of the invention, the transistor may be a bipolar transistor, in particular, a positive-negative-positive (PNP) bipolar transistor, configured to switch from a so-called on-state, corresponding to the first state, to a so-called off-state, corresponding to the second state, and wherein the input electrode of the transistor is a base of the bipolar transistor and the output electrode of the transistor is a collector of the bipolar transistor.

According to one embodiment of the invention, the transistor may be a Metal Oxide Semiconductor Field Effect Transistor (MOSFET) wherein the input electrode of the transistor is a gate of the MOSFET and the output electrode of the transistor is a drain of the MOSFET.

According to one embodiment of the invention, the moisture sensor may comprise first resistors of different values.

It is possible to improve the sensitivity and quality of the moisture detection by using first resistors of different values.

According to one embodiment of the invention, the plurality of pairs of electrodes may be distributed by pre-defined zones of the first face, and the value of each first resistor may be relative to a pre-defined zone of the first face.

Thus, it is possible to determine both the presence and also the distribution of liquid on the various pre-defined zones of the moisture sensor.

For example, a first resistance value associated to pairs of electrodes arranged centrally on the first face may be different from a first resistance value associated to a pair of electrodes arranged peripherally on the first face. This makes it possible to determine whether the center of the first face is wetter or not than its periphery.

According to one embodiment of the invention, the plurality of first means of detection may be encased in an encapsulation resin.

The encapsulation resin ensures a tight seal and thus prevents short circuits.

According to one embodiment of the invention, the support substrate may comprise at least one through orifice allowing a fluid to flow between the first and second faces.

The presence of at least one through orifice allows the liquid to pass through the support substrate, that is thus not made impermeable. The through orifice allows the liquid to be "vertically" diffused through the support substrate in a direction extending from the first face to the second face.

According to one embodiment of the invention, the electrodes of the plurality of pairs of electrodes may be arranged on the first face in at least two directions contained in a plane of the first face, in particular, cross-shaped, in particular, cross-shaped with at least six points.

The cross-shaped or star-shaped arrangement of the electrodes facilitates the "horizontal" diffusion of the liquid in the plane of the first face. Indeed, the electrodes, depending on their arrangement, could block the propagation of the liquid in the plane of the first face.

According to one embodiment of the invention, for each pair of electrodes, each electrodes of the pair of electrodes may be electrically connected by a metallized hole formed between the first face and the second face to a corresponding first means of detection that is arranged on said second face.

According to one embodiment of the invention, the support substrate may be a flexible layer capable of being curved, in particular, less than 300 micrometers thick, more particularly, less than 150 micrometers thick.

According to one embodiment of the invention, the moisture sensor may further comprise a microchip on the second face configured to transmit the data to a third party, in particular, by radio frequency communication.

Thus, the moisture sensor is adapted to be able to process the data collected by the means of detection and to communicate them by radio frequency.

According to one embodiment of the invention, the first face may further comprise a radio antenna.

Thus, the data from the moisture detection system may be communicated to a third-party device via radio frequency.

The fact that the radio antenna is arranged on the first face, i.e. on the face provided with the electrodes, both saves space and also facilitates the mounting and electrical connections in the support substrate.

According to one embodiment of the invention, the radio antenna may be arranged around a plurality of pairs of electrodes.

Thus, it is possible to easily manufacture moisture sensors in different forms, regardless of, for example, the distance between electrodes.

According to one embodiment of the invention, the support substrate may further comprise at least another pair of detecting electrodes and at least a second means of detection of a quantity other than moisture, and said pair of detecting electrodes being electrically connected to the second means of detection such that the moisture sensor is further configured to measure a quantity other than moisture, in particular, temperature, pressure, pH, or the presence of a chemical species.

The moisture sensor may thus advantageously allow the detection of physical, chemical or even electrochemical quantities, in addition to the detection of moisture. The use of different separate sensors may thus be avoided by combining a plurality of detection means in the moisture sensor.

The second detection means may be embedded in the encapsulation resin.

The aim of the present invention also relates to the use of the moisture sensor described above, in a wound dressing wherein the plurality of pairs of electrodes of the moisture sensor is arranged in the wound dressing to be in contact with a liquid from a wound.

The use of the moisture sensor in a wound dressing advantageously makes it possible to avoid the need to measure the resistance (or impedance or electrical conductivity) of blood, exudate, pus, etc., that is particularly dependent on each wound and patient.

The aim of the present invention is also achieved by means of a method for detecting moisture by means of a moisture sensor according to one of the embodiments mentioned above, comprising the following steps of: a) measuring the equivalent resistance of the first resistors of the plurality of the first means of detection of the moisture sensor that is dependent on the number of transistors switched in one of the first or second states, then, b) from the equivalent resistance value measured, deducing the presence of liquid on the first face provided with the electrodes.

The method of detecting moisture according to the present invention advantageously makes it possible to avoid the need to measure the resistance (or the impedance or electrical conductivity) of the liquid, that depends on the composition and properties specific to each liquid, in particular, to each exudate in the case of an application of the moisture sensor in a wound dressing.

The embodiments may be combined to form more advantageous embodiment variants of the present invention.

BRIEF DESCRIPTION OF THE DRAWINGS

The invention and its advantages will now be explained in more detail below by means of preferred embodiments and, in particular, by making reference to the accompanying figures, wherein.

DETAILED DESCRIPTION

The invention will now be described in more detail using advantageous embodiments by way of example and in reference to the drawings. The embodiments described are simply possible configurations and it should be kept in mind that the individual features such as described above can be supplied independently from each other or can be absolutely omitted during the implementation of the present invention.

Figure 1:
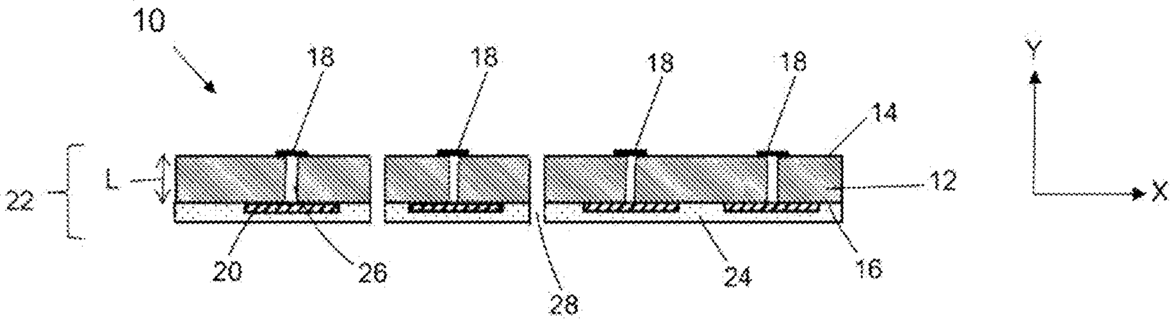
FIG. 1 is a schematic cross-sectional view of a moisture sensor according to one embodiment of the present invention.

FIG. 1 is a schematic cross-sectional view of a moisture sensor 10 according to one embodiment of the present invention.

The moisture sensor 10 is intended to detect the presence and position of a liquid on a surface.

The moisture sensor 10 comprises a support substrate 12.

The support substrate 12 is a flexible layer capable of being curved, in particular, to conform to the curvature of an element.

For example, in the case where the moisture sensor 10 is integrated into a wound dressing, the flexible support substrate 12 is adapted to be curved so as to conform to the shape of a part of a human body to which the said wound dressing is intended to be applied.

The support substrate 12 can be made of epoxy glass, polyimide, polyethylene terephthalate (PET), polyethylene naphthalene (PEN) or other.

The support substrate 12 has a thickness L of less than 300 micrometers, in particular, less than 150 micrometers. It is noted that the thickness L corresponds to the thickness of the support substrate 12 only, without taking into consideration the thickness of any layer other than the substrate 12 itself, such as an encapsulant.

The support substrate 12 comprises a first face 14 and a second face 16, geometrical opposite to the first face 14 according to a Y-axis of the Cartesian co-ordinate system.

The first face 14 is provided with a plurality of electrodes 18 configured to be in contact with a liquid.

The electrodes 18 are preferably made of a copper alloy plated with gold or nickel-gold, or of aluminum, bronze, gold, plated with gold or other.

The second face 16 is provided with a plurality of means of detection 20. As described below, the means of detection 20 are connected to each other in parallel. The means of detection 20 may also be referred to below as “first means of detection 20”. The first means of detection 20 are configured to detect moisture. As explained below, in a variant, the support substrate 12 may also comprise one or more second means of detection (not shown) configured to detect a quantity other than moisture, among others, to measure temperature, pressure, pH, or the presence of a certain chemical species.

The entire support substrate 12, electrodes 18 and means of detection 20 are constituted by an electrical printed circuit board 22.

The electrical printed circuit board 22 may be manufactured by well-known methods for the manufacture of flexible printed circuit boards, i.e., flexible ones, also known as “flex PCBs” or “flex circuits”, particularly, within the field of smart cards. In particular, the electrical printed circuit board 22 can be manufactured by the manufacturing method disclosed in French patent application FR 3013504 A1.

According to such a manufacturing method, a material composed of the support substrate layer 12 and at least one sheet of electrically conductive material is supplied on its first face 14. The conductive material is, for example, copper, aluminum, or an alloy of copper or aluminum. The second face 16 of the support substrate 12 is coated with an adhesive material (not shown). The support substrate 12 coated with the adhesive and conductive material is perforated, e.g., by mechanical punching or laser, to form holes 26 and optionally lateral openings (perforations) used for guiding a strip in a coil-to-coil method. A second sheet of electrically conductive material is then laminated to the second face 16 of the support substrate 12. This sheet covers the adhesive and the holes 26. The holes 26 are then called “blind” holes because they are closed on one face by the metal sheet.

Alternatively, a material composed of the support substrate 12 and two layers of conductive material is supplied. This material is perforated, for example, by mechanical punching or by laser, to form holes 26 that are then called “through” orifices.

Regardless of whether the holes 26 are formed so as to be through orifices or not, one or more layers of electrically conductive material are thus electrodeposited in the holes 26. Patterns are then made by photolithography on the two sheets of electrically conductive material by deposition, insolation and revelation of a photosensitive resin.

A chemical pattern engraving step makes it possible to produce, among others, the electrodes 18 on the face 14 and the electrical circuit 22 making it possible to connect the means of detection 20 on the face 16.

The resin protecting the patterns during engraving is chemically removed and top coats (e.g., nickel and gold) are optionally deposited electrochemically or chemically on the engraved patterns and in the metallized holes 26.

The electronic components used in the means of detection 20 are then assembled on the electrical circuit 22.

In order to electrically isolate the electrical circuit 22 and the means of detection 20 from a liquid, the electrical circuit 22 and the means of detection 20 are encased in an encapsulation resin 24 at the second face 16. The encapsulation resin 24 ensures a tight seal at the second face 16 and prevents short circuits.

The encapsulation resin 24 can be a silicone, polyamide, epoxy resin or other.

As shown in FIG. 1, each of the electrodes 18 is electrically connected to a corresponding means of detection 20 by a metallized hole 26 passing through the support substrate 12 from the first face 12 to the second face 16.

In other words, each of the metallized holes 26 makes it possible to electrically connect an electrode 18 to a means of detection 20.

As explained above with respect to the manufacturing method, the holes 26 are metallized by a deposit of copper, nickel and/or gold.

As shown in FIG. 1, the electrical circuit 22 is provided with at least one through orifice 28 allowing a fluid to flow between the first face 14 and the second face 16. Each through orifice 28 thus extends from the first face 14 to the second face 16 through the electrical circuit 22 and the encapsulation resin 24.

Each through orifice 28 may be made by punching or piercing the encapsulation resin and the electrical circuit 22.

Figure 2:
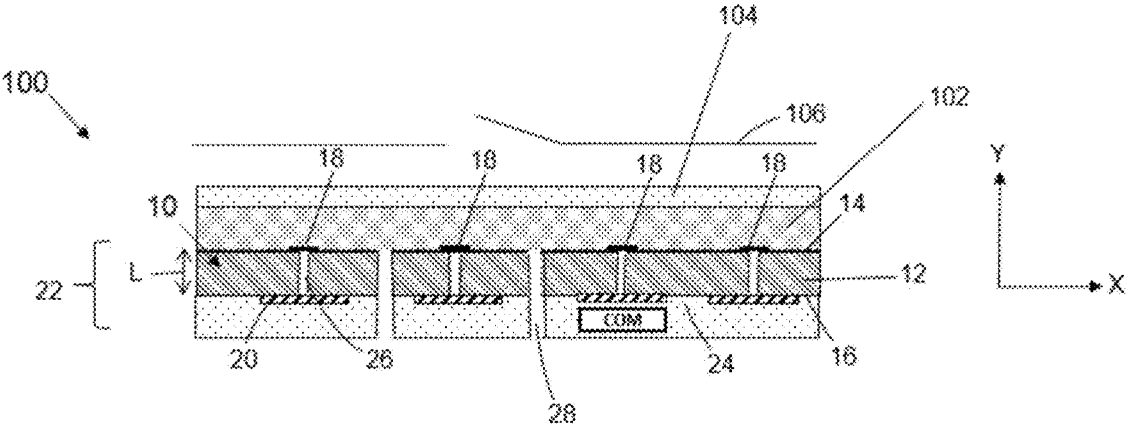
FIG. 2 is a schematic cross-sectional view of a wound dressing wherein the moisture sensor is integrated according to one embodiment shown in FIG. 1.

FIG. 2 schematically shows the integration of a moisture sensor 10, according to the embodiment shown in FIG. 1, in a wound dressing 100. The wound dressing 100 comprises the moisture sensor 10 and a communication module COM.

The elements with the same reference numerals already used for the description of FIG. 1 will not be described again in detail, and reference is made to their descriptions above.

The wound dressing 100 comprises a plurality of layers. Some layers have been intentionally omitted from the schematic representation in FIG. 2 for the sake of clarity and simplification of the drawing.

An absorbent layer 102 is supplied on the first face 14 of the support substrate 12 of the moisture sensor 10. The absorbent layer 102 may consist of a plurality of layers (not shown). The absorbent layer 102 comprises an application face 104 configured to be applied to a wound. The absorbent layer 102 is thus configured to absorb a liquid, in particular, an exudate, from a wound on which the wound dressing 100 is intended to be applied. The exudate is a liquid that oozes from a wound. The exudate contains water and electrolytes, among others. The electrodes 18 being arranged on the first face 14, the electrodes 18 are configured to be in contact with a liquid absorbed by the absorbent layer 102.

As explained in reference to FIG. 1, the encapsulation resin 24 ensures a tight seal at the second face 16 and prevents short circuits. But, the tight seal of the second face 16 has the effect of making the substrate 12 non-permeable. However, it is necessary that the fluid from the wound is able to diffuse through the wound dressing 100, among others, vertically, i.e., in a direction of depth of the wound dressing 100 along the Y-axis shown in FIG. 2. For this purpose, the through orifices 28 allow fluid communication between the first face 14 and the second face 16. The distribution of the through orifices 28 may be regular or vary between a central zone of the wound dressing 100 and a peripheral part of the wound dressing 100.

To communicate with at least one third-party device, the wound dressing 100 comprises the communication module COM. In the example of the embodiment shown in FIG. 2, the communication module COM is encapsulated in resin 24 so that it is protected. Alternatively, the communication module COM may be partially encapsulated.

The communication module COM may comprise an integrated circuit, e.g., a processor, and an antenna. The communication module COM may, among others, be a Near Field Communication (NFC) module.

In FIG. 2, the communication module COM is schematically represented by a block, without the integrated circuit or antenna being visible, and without this representation being limiting. The communication module COM may be arranged so that all of its elements are on one face (the first face 14 or the second face 16), or distributed on both faces 14 and 16. A possible configuration of the communication module COM may comprise an encapsulation of its integrated circuit (not shown in FIG. 2) in resin 24, mounted on the second face 16, and an installation of its antenna (not shown in FIG. 2) on the first face 14 (possibly without encapsulation), as it will be described subsequently in reference to FIGS. 3 and 4. A through connection between the antenna and the integrated circuit (not shown in FIG. 2) of the communication module COM may be used.

Finally, FIG. 2 shows that the application face 104 is protected by detachable protective film 106. The wound dressing 100 is designed to be packaged sterile until use.

FIG. 2 shows a wound dressing 100 comprising the support substrate 12, the first face 14 of which is configured to be applied, directly or indirectly, to a wound. The first face 14 is provided with a plurality of electrodes 18 configured to be in contact with a liquid from the wound. The second face 16, that is geometrically opposite to the first face (14), comprises the plurality of means of detection 20 connected in parallel. Each means of detection 20 comprises a switching means (not visible in FIG. 2), such as a transistor, associated to two electrodes 18 forming a pair of electrodes (shown in FIGS. 3 and 4 by reference 30). Each switching means is configured to switch from a first state to a second state when an electric current passes between the pair of electrodes associated to said switching means. The moisture of the wound dressing 100, in particular, the absorbent layer 102, may be determined from the number of switching means switched in one of said states compared to those switched in the other state.

The determination of moisture according to the present invention is further detailed in reference to FIGS. 3 to 7.

It should be noted that the wound dressing 100 may also comprise at least another measuring sensor of a different quantity than moisture. In this case, the support substrate 12 of the moisture sensor 10 comprises at least another pair of detecting electrodes, in particular, distinct from the plurality of pairs of electrodes 30 described above, and at least a second means of detection (not shown) of a quantity other than moisture, said pair of detecting electrodes being electrically connected to the second means of detection. Thus, the moisture sensor 10 in the wound dressing 100 is also configured to measure a quantity other than moisture, in particular, temperature, pressure, pH or the presence of a chemical species.

Figure 3:
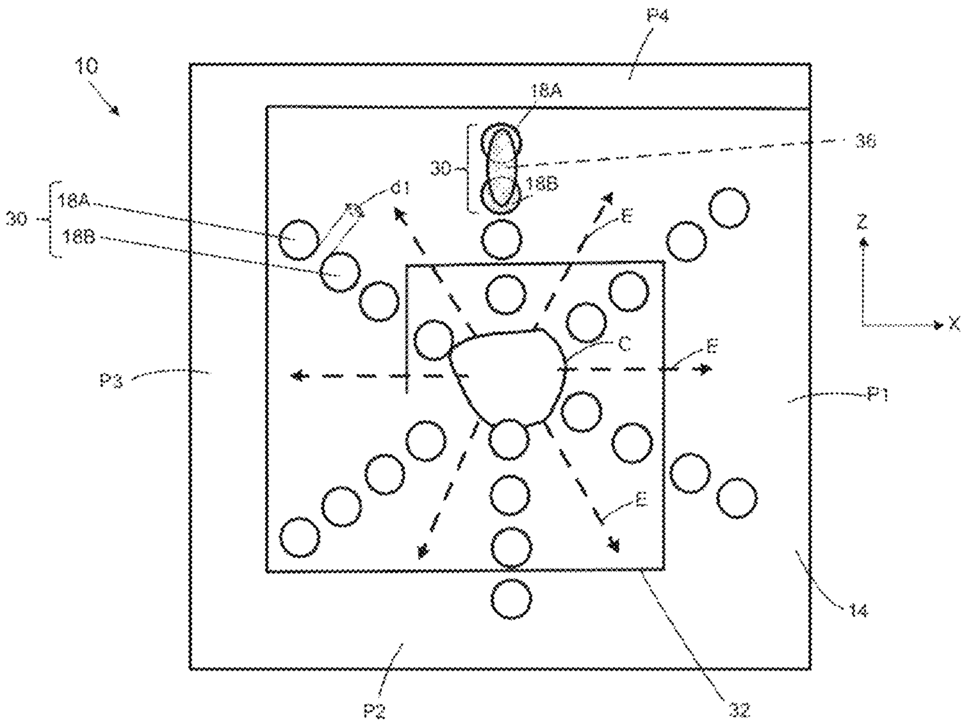
FIG. 3 is a schematic view of a first face of a moisture sensor according to one embodiment of the present invention.

FIG. 3 shows a schematic view of the first face 14 of the moisture sensor 10 according to an embodiment of the present invention.

The elements with the same reference numerals already used for the description of FIG. 1 will not be described again in detail, and reference is made to their descriptions above.

The first face 14 of the moisture sensor 10 comprises the plurality of electrodes 18.

It is noted that the first face 14 does not comprise any electronic components, these are arranged on the second face 16 and encased in the encapsulation resin 24.

According to the embodiment shown in FIG. 3, the electrodes 18 are circular in shape. In one variant, the form of the electrodes 18 may be different, e.g., square, rectangular, oval, triangular, spiral, cross-shaped or star-shaped.

Preferably, the electrodes 18, 18A, 18B have a contact surface of between 0.5 $mm^2$ and 8 $mm^2$.

The electrodes 18 are arranged by pair of electrodes 30.

A pair of electrodes 30 is formed by two electrodes 18A, 18B arranged in close proximity to each other without touching each other. The electrodes 18A, 18B constituting a pair of electrodes 30 are spaced apart by an inter-electrode distance d1. The distance d1 may be varied depending on the embodiment. In particular, the distance d1 is between 100 micrometers and 2 millimeters. The inter-electrode distance d1 within a pair of electrodes 30 may vary between different pairs of electrodes 30 of the moisture sensor 10.

Figure 4:
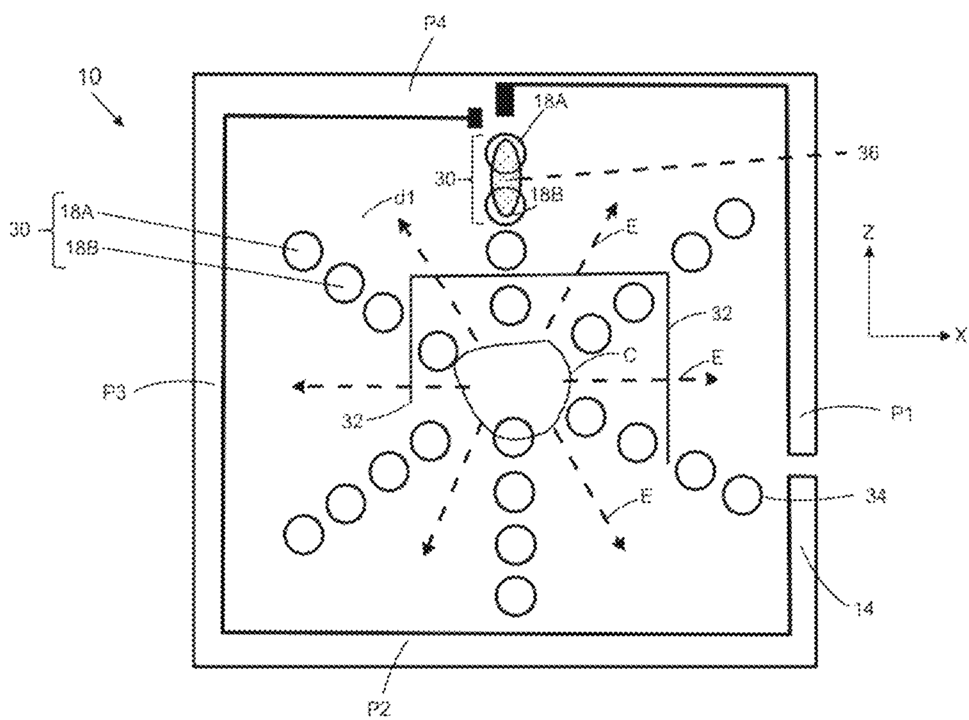
FIG. 4 is a schematic view of the moisture sensor in FIG. 3 comprising a radio frequency antenna according to one variant of the invention.

As explained in more detail in reference to FIG. 4, a pair of electrodes 30 is associated to each means of detection 20.

In the example shown in FIG. 3, the plurality of electrodes 18 is arranged cross-shaped on the first face 14, so as to form a cross with six points. In one variant (not shown), the plurality of electrodes 18 is arranged according to a cross-shaped configuration with eight points. The number of points is not limiting.

The cross-shaped configuration makes it possible to facilitate the diffusion and propagation of the liquid (indicated by the dotted arrows E in FIG. 3) from the center in the plane (XZ) of the first face 14, particularly, from a central zone C of the first face 14 to peripheral zones P1, P2, P3, P4 of the first face 14.

Other arrangements of the electrodes 18 to detect the diffusion of liquid in all directions of the plane are possible (in circles, concentrically, etc.).

As shown in FIG. 3, the first face 14 also comprises a radio antenna 32. The fact that the radio antenna 32 is arranged on the first face 14, i.e. on the face 14 that is also provided with the electrodes 18, both saves space in the moisture sensor 10 and also facilitates the mounting and electrical connections of the support substrate 12.

The radio antenna 32 is electrically connected to the circuit board 22 of the second face 16 by at least one metallized hole (not visible in FIG. 3). In particular, the antenna may be electrically connected to an integrated circuit of the communication module COM.

In the example in FIG. 3, the radio antenna 32 has a spiral shape with arms passing between the electrodes 18.

In a variant, shown in FIG. 4, the moisture sensor 10 may be provided with a radio antenna 34 that is arranged around the plurality of pairs of electrodes 30. The radio antenna 34 is electrically connected to the printed circuit board 22 of the second face 16 by at least one metallized hole (not visible in FIG. 4). The arrangement as shown in FIG. 4 makes it easier to overcome the shape factor to be taken into consideration when manufacturing a moisture sensor 10 of different in-plane (XZ) dimensions.

The antennae 32, 34 allow wireless connection with a third-party device (not shown) of the moisture sensor 10, particularly, by means of an integrated circuit of the communication module COM that will be connected to antennae 32, 34.

It is noted that only the antenna differs between the representations of the moisture sensor 10 shown in FIGS. 3 and 4.

The moisture sensor 10 is sensitive to the extent of the first face 14 wetted by a liquid. Gradually, as the liquid flows, it spreads to the first face 14, e.g., from the central zone C. Thus, the liquid 36 may be present between two electrodes 18A, 18B of a pair of electrodes 30. The presence of liquid 36 between two electrodes 18A, 18B of a pair of electrodes 30 electrically connects electrodes 18A, 18B to each other. The passage of an electric current between electrodes 18A, 18B generates a short circuit between said electrodes 18A, 18B of the pair of electrodes 30. The short circuit of electrodes 18A, 18B is used by the means of detection 20 to determine the presence and distribution of liquid on the first face 14, as further described below in reference to the following figures.

Figure 5:
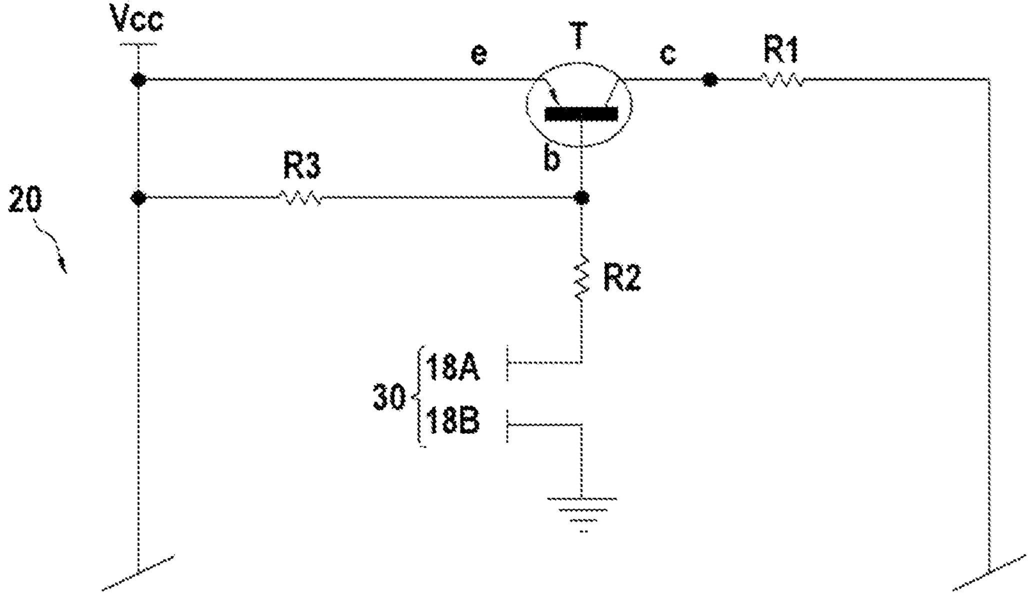
FIG. 5 schematically shows a means of detection according to one embodiment of the present invention.

FIG. 5 schematically shows a means of detection 20 according to one embodiment of the present invention.

The elements with the same reference numerals already used for the description of FIGS. 1 to 4 will not be described again in detail, and reference is made to their descriptions above.

Each means of detection 20 according to the present invention comprises a transistor T associated to a pair of electrodes 30 formed by two electrodes 18A, 18B of the plurality of electrodes 18.

In particular, the transistor T is a positive-negative-positive (PNP) bipolar transistor.

In one variant, the transistor T is a Metal Oxide Semiconductor Field Effect Transistor (MOSFET), and the circuit described below may be adapted accordingly. In particular, the base, collector, and transmitter of the bipolar transistor correspond to the gate, source, and drain of the MOSFET, respectively.

The transistor T is configured to switch from a first state, wherein the transistor T is at an on-state to a second state, wherein the transistor T is at an off-state. In fact, the transistor T operates in the saturation zone.

The transmitter e of the transistor T is connected to the supply voltage Vcc.

The collector c of the transistor T is connected in series to a first resistor R1, e.g., a 1.2 M Ohm resistor R1. The first resistors R1 of each means of detection 20 are connected in parallel to each other in the electrical circuit 22.

In one variant, the first resistors R1 of the moisture sensor 10 have different values. For example, the value of the first resistors R1 arranged at the central zone C (see FIGS. 3 and 4) of the first face 14 is different from the value of the first resistors R1 arranged at the peripheral zones P1, P2, P3, P4 (see FIGS. 3 and 4) of the first face 14.

The base b of the transistor T is connected to a second resistor R2, e.g., a 20K Ohm resistor R2. The resistor R2 is used to change the state of the transistor T when the liquid contacts electrodes 18A, 18B.

The second resistor R2 is connected in series to an electrode 18A of the pair of electrodes 30.

The other electrode 18B of the pair of electrodes 30 is earthed, i.e. at a reference potential, usually at 0 Volt.

A third electrode R3, e.g., a 200K Ohm resistor R3, is connected to the supply voltage Vcc and the base of the transistor T, as shown in FIG. 5.

It is noted that the means of detection 20 according to the present invention is not strictly limited to the electrical circuit diagram of the embodiment shown in FIG. 5.

In the embodiment shown in FIG. 5, the transistor T is in the on-state when the electrodes 18A, 18B are dry, i.e. when an electric current cannot flow through the pair of electrodes 30, in the absence of a conductor between electrodes 18A, 18B.

The transistor T switches to the off-state when liquid connects the electrodes 18A, 18B, thus earthing the base b of the transistor T. In fact, the presence of liquid between the electrodes 18A, 18B of each pair of electrodes 30 changes the voltage until the voltage reaches a voltage threshold at which the transistor T is configured to automatically switch from a first state to a second state, in particular, from an on-state to an off-state. The transistor T thus operates in switching, i.e. a type of "all or nothing" operation (or switch). The voltage across the first resistor R1 in series with the collector of the transistor T thus varies from one level to another, depending on the state of the transistor T, as opposed to a gradual evolution of the voltage.

The voltage across the first resistor R1 of each means of detection 20 is therefore representative of the state of the corresponding transistor T. The state (on-state or off-state) of the transistor T is representative of the presence (or absence) of liquid between the pair of electrodes 30 of each means of detection 20. The first resistors R1 are mounted in parallel in electrical circuit 22.

Figure 6:
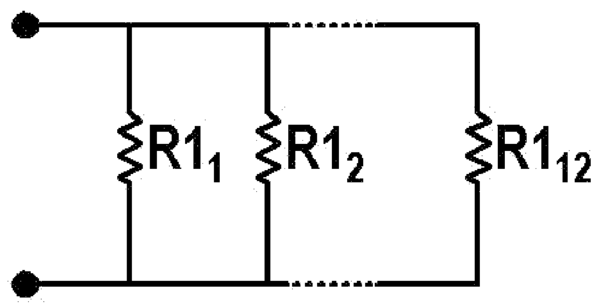
FIG. 6 schematically shows the connection of the first resistors in parallel with the moisture detection system according to the present invention.

FIG. 6 schematically shows the parallel connection of the first resistors R1 of the moisture sensor 10 that comprises, in the example illustrated in FIGS. 3 and 4, twelve resistors R1 ($R1_1$ to $R1_{12}$) in parallel and twenty-four electrodes 18 forming twelve pairs of electrodes 30. The number of electrodes, and therefore of resistors R1, is not limiting.

To determine the presence and distribution of liquid on the face 14, the moisture sensor 10 is configured to measure the equivalent resistance Req of the first resistors R1 in parallel. The equivalent resistance Req of the first resistors R1 in parallel may be measured at a pre-defined time interval. From the equivalent resistance Req, it is possible to deduce the number of first resistors R1 associated to a transistor T that has been switched by the presence of liquid between the electrodes 18A, 18B of a pair of electrodes 30. Thus, it is possible to deduce the number of pairs of electrodes 30 connected by the presence of liquid 34 between the electrodes 18A, 18B of the pair of electrodes 30. The number of pairs of electrodes 30 connected is relative to the surface wetted by the liquid 36.

Figure 7:
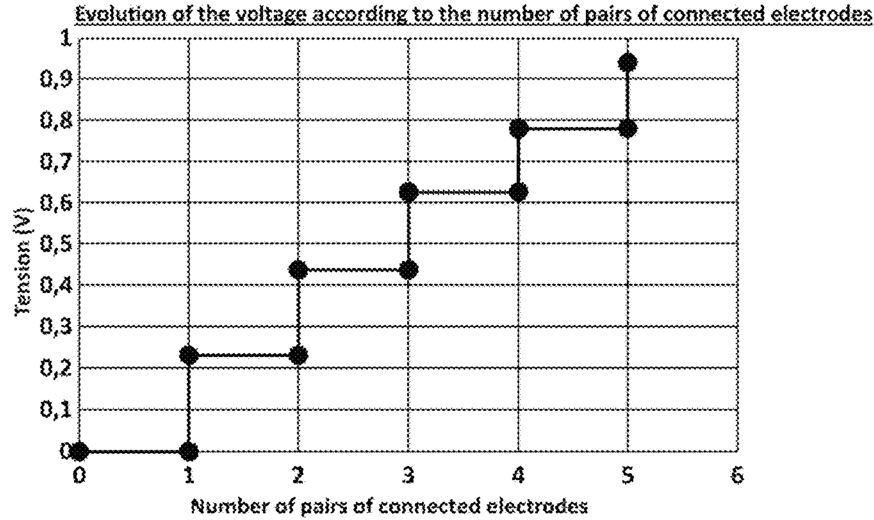
FIG. 7 shows the evolution of the voltage according to the number of pairs of connected electrodes.

FIG. 7 shows a graphical representation of the voltage evolution according to the number of pairs of connected electrodes 30 by the presence of liquid 36 between the electrodes 18A, 18B of the pair of electrodes 30. It can be seen that the voltage increases in stages with each pair of connected electrodes (indicated on the x-axis). The evolution of the voltage in stages is especially dependent on the value of the resistors R2 and R3.

The moisture sensor 10 is thus sensitive to the number of transistors T switched in an on-state (respectively in an off-state) compared to those switched in an off-state (respectively in an on-state). The moisture sensor 10 according to the present invention operates independently of the value of the electrical conductivity of the liquid between the electrodes 18A, 18B of each pair of electrodes 30.

Thus, a method for measuring moisture by means of a moisture sensor 10 according to the present invention consists of measuring the equivalent resistance Req of the first resistors R1 that is dependent on the number of switched transistors T, and, from the value of the equivalent resistance measured, deducing the presence of liquid on the first face 14 provided with the electrodes 18.

It is noted that the transistors T are compatible with a microchip, among others, to measure the equivalent resistance Req and to process the data measured. The microchip may be configured to transmit data to a third-party device via radio frequency communication or Near Field Communication (NFC), among others, by means of antenna 32 or 34. Thus, the moisture sensor 10 is adapted to be able to process the data collected by the means of detection and communicate them by radio frequency. This data comprises at least one piece of information relating to the moisture detected by the moisture sensor 10, e.g., a moisture value, a value relating to the surface of the first face 14 covered by liquid (e.g., a number of electrode), or a percentage relating to the moisture.

In the case where the moisture sensor 10 is integrated in a wound dressing 100, as shown in FIG. 2, the moisture sensor 10 advantageously makes it possible to detect the presence and extent of the exudate in the absorbent layer 102 of the wound dressing 100 according to the principle described in reference to FIGS. 5 to 7.

Figure 8:
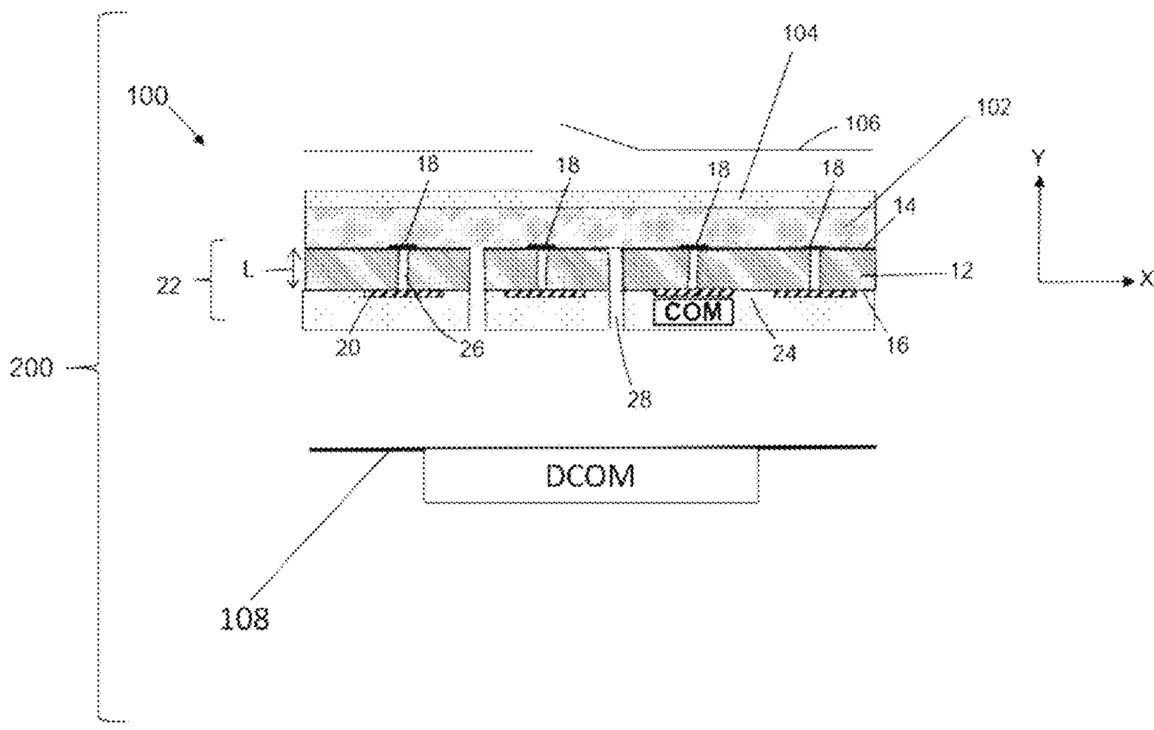
FIG. 8 shows a system comprising a wound dressing as shown in FIG. 2 and a communication device.

FIG. 8 shows a system 200 comprising a wound dressing 100, as shown in FIG. 2, and a communication device DCOM.

The wound dressing 100 also comprises a protective layer 108, that is supplied on the side opposite to the application face 104. The protective layer 108 may also be referred to, by the person skilled in the art, as a support layer 108. It is this layer 108 that, in a wound dressing, is waterproof but breathable, in a manner known to the person skilled in the art.

In the system 200, a communication device DCOM is removably attached to the protective layer 108 of the wound dressing 100, e.g., by means of an adhesive, a hook and loop textile system, or a pocket. Thus, the communication device DCOM may be detached to be reused, while the 100 wound dressing must be discarded after use. The communication device DCOM, being removable, acts as a "patch" that will be attached only when the system 200 is on a user, and then kept for another wound dressing 100 when this one is changed. This limits the quantity of e-waste.

The communication device DCOM may communicate with the communication module COM via Near Field communication, e.g., to retrieve moisture information and store it in a memory (not shown) of the communication device DCOM.

The communication device DCOM comprises a power supply battery (not shown), and supplies the wound dressing 100 of the system 200 with electrical energy via magnetic induction.

Figure 9:
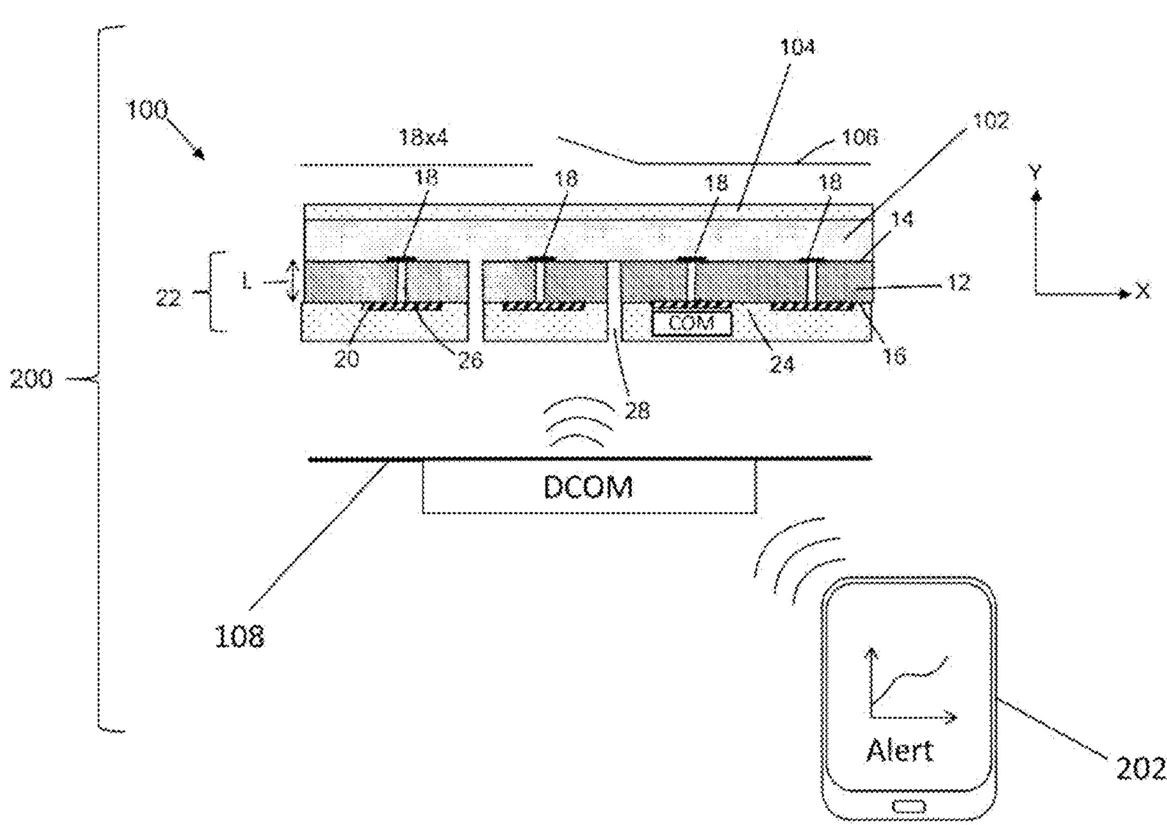
FIG. 9 shows the system illustrated in FIG. 8 and a user terminal.

As shown in FIG. 9, the communication device DCOM may also be capable of communicating with a user terminal 202 (e.g., via Bluetooth [Low Energy] communication), such that a moisture data detected by the moisture sensor wound dressing 100 of the system 200 may be received and displayed on user terminal 202.

By way of indication, the communication device DCOM may transmit an alert signal that will be displayed on the user terminal 202, for example, to indicate that a rate of change in moisture exceeds a given threshold.

LIST OF REFERENCES

10: moisture sensor
12: support substrate

14: first face
16: second face
18: electrodes
20: means of detection
22: electrical printed circuit board
24: encapsulation resin
26: metallized hole
28: through orifice
30: pair of electrodes
32: antenna
34: antenna
36: liquid
100: wound dressing
102: absorbent layer
104: application face
106: detachable protective film
108: protective layer
200: system
202: user terminal
COM: communication module
DCOM: communication device
b: base
c: collector
C: central zone
D1: inter-electrode distance
L: thickness
e: transmitter
E: flow direction
P1, P2, P3, P4: peripheral zones
R1: first resistor
R2, R3: resistors
Req: equivalent resistance
T: transistor
Vcc: supply voltage
X, Y, Z: Cartesian co-ordinate system

The invention claimed is:

1. A moisture sensor comprising a support substrate having a first face and a second face, geometrically opposite to the first face, and wherein:

the first face is provided with a plurality of pairs of electrodes configured to be in contact with a liquid, and the second face comprises a plurality of first means of detection connected to each other in parallel, and each first means of detection comprises a transistor (T) associated with a pair of electrodes, and said transistor (T) of each first means of detection is configured to switch from a first state to a second state when an electric current passes between electrodes of the pair of electrodes associated to the transistor (T), an electrode of the pair of electrodes being electrically connected in series to an input electrode (b) of the transistor (T) and the other electrode of the pair of electrodes being electrically connected to a fixed potential, in particular, to an earth potential, and an output electrode (c) of the transistor (T) being electrically connected in series with a first resistor (R1), such that the moisture sensor is sensitive to the equivalent resistance (Req) of said first resistors (R1) of the plurality of the first means of detection.

2. The moisture sensor according to claim 1, wherein the transistor (T) is a bipolar transistor (T), in particular, a positive-negative-positive (PNP) bipolar transistor, configured to switch from a so-called on-state, corresponding to the first state, to a so-called off-state, corresponding to the second state, and wherein the input electrode (b) of the transistor (T) is a base (b) of the bipolar transistor (T) and the output electrode (c) of the transistor (T) is a collector of the bipolar transistor (T).

3. The moisture sensor according to claim 1, wherein the transistor (T) is a Metal Oxide Semiconductor Field Effect Transistor (MOSFET) wherein the input electrode (b) of the transistor (T) is a gate of the MOSFET and the output electrode (c) of the transistor (T) is a drain of the MOSFET.

4. The moisture sensor according to claim 1, comprising first resistors (R1) of different values.

5. The moisture sensor according to claim 4, wherein the plurality of pairs of electrodes is distributed by predefined zones of the first face, and the value of each first resistor (R1) is relative to a predefined zone of the first face.

6. The moisture sensor according to claim 1, wherein the plurality of the first means of detection is encased in an encapsulation resin.

7. The moisture sensor according to claim 1, wherein the support substrate comprises at least one through orifice allowing a fluid to flow between the first face and the second face.

8. The moisture sensor according to claim 1, wherein the electrodes of the plurality of pairs of electrodes are arranged on the first face in at least two directions contained in a plane of the first face, in particular, cross-shaped, in particular, cross-shaped with at least six points.

9. The moisture sensor according to claim 1, wherein, for each pair of electrodes, each of the electrodes of the pair of electrodes is electrically connected by a metallized hole formed between the first face and the second face to a corresponding first means of detection that is arranged on said second face.

10. The moisture sensor according to claim 1, wherein the support substrate is a flexible layer capable of being curved, in particular, less than 300 micrometers thick, more particularly, less than 150 micrometers thick.

11. The moisture sensor according to claim 1, further comprising a microchip at the second face configured to transmit data to a third-party device.

12. The moisture sensor according to claim 1, wherein the first face further comprises a radio antenna.

13. The moisture sensor according to claim 12, wherein the radio antenna is arranged around the plurality of pairs of electrodes.

14. The moisture sensor according to claim 1, wherein the support substrate further comprises at least another pair of detecting electrodes and at least a second means of detection of a quantity other than moisture, and said pair of detecting electrodes being electrically connected to the second means of detection such that the moisture sensor is further configured to measure a quantity other than moisture, in particular, temperature, pressure, pH, or the presence of a chemical species.

15. A use of a moisture sensor in a wound dressing, wherein the moisture sensor comprises a support substrate having a first face and a second face, geometrically opposite to the first face, and wherein:

the first face is provided with a plurality of pairs of electrodes configured to be in contact with a liquid, and the second face comprises a plurality of first means of detection connected to each other in parallel, and each first means of detection comprises a transistor associated with a pair of electrodes, and said transistor of each first means of detection is configured to switch from a first state to a second state when an electric current passes between electrodes of the pair of electrodes associated to the transistor, an electrode of the pair of electrodes being electrically connected in series to an input electrode of the transistor and the other electrode of the pair of electrodes being electrically connected to a fixed potential, in particular, to an earth potential, and an output electrode of the transistor being electrically connected in series with a first resistor, such that the moisture sensor is sensitive to the equivalent resistance of said first resistors of the plurality of the first means of detection; and wherein the plurality of pairs of electrodes of the moisture sensor is arranged in the wound dressing to be in contact with a liquid from a wound.

16. A method for detecting moisture by means of a moisture sensor wherein the moisture sensor comprises a support substrate having a first face and a second face, geometrically opposite to the first face, wherein:

the first face is provided with a plurality of pairs of electrodes configured to be in contact with a liquid, and the second face comprises a plurality of first means of detection connected to each other in parallel, and each first means of detection comprises a transistor associated with a pair of electrodes, and said transistor of each first means of detection is configured to switch from a first state to a second state when an electric current passes between electrodes of the pair of electrodes associated to the transistor, an electrode of the pair of electrodes being electrically connected in series to an input electrode of the transistor and the other electrode of the pair of electrodes being electrically connected to a fixed potential, in particular, to an earth potential, and an output electrode of the transistor being electrically connected in series with a first resistor, such that the moisture sensor is sensitive to the equivalent resistance of said first resistors of the plurality of the first means of detection; and wherein the method comprises the following steps of:

a) measuring the equivalent resistance (Req) of the first resistors (R1) of the plurality of the first means of detection of the moisture sensor that is dependent on the number of transistors (T) switched in one of the first or second states, then, b) from the equivalent resistance value measured, deducing the presence of liquid on the first face provided with the electrodes.

17. The use of the moisture sensor of claim 15, wherein the transistor is a bipolar transistor, in particular, a positive-negative-positive (PNP) bipolar transistor, configured to switch from a so-called on-state, corresponding to the first state, to a so-called off-state, corresponding to the second state, and wherein the input electrode of the transistor is a base of the bipolar transistor and the output electrode of the transistor is a collector of the bipolar transistor.

18. The use of the moisture sensor of claim 15, wherein the transistor is a Metal Oxide Semiconductor Field Effect Transistor (MOSFET) wherein the input electrode of the transistor is a gate of the MOSFET and the output electrode of the transistor is a drain of the MOSFET.

19. The method of claim 16, wherein the transistor is a bipolar transistor, in particular, a positive-negative-positive (PNP) bipolar transistor, configured to switch from a so-called on-state, corresponding to the first state, to a so-called off-state, corresponding to the second state, and wherein the input electrode of the transistor is a base of the bipolar transistor and the output electrode of the transistor is a collector of the bipolar transistor.

20. The method of claim 16, wherein the transistor is a Metal Oxide Semiconductor Field Effect Transistor (MOSFET) wherein the input electrode of the transistor is a gate of the MOSFET and the output electrode of the transistor is a drain of the MOSFET.

* * * * *